US012590287B2

(12) United States Patent
Soerensen et al.

(10) Patent No.: US 12,590,287 B2
(45) Date of Patent: Mar. 31, 2026

(54) LACTIC ACID BACTERIAL STRAIN WITH IMPROVED TEXTURIZING PROPERTIES

(71) Applicant: Chr. Hansen A/S, Hoersholm (DK)

(72) Inventors: Kim Ib Soerensen, Hoersholm (DK);
Mette Pia Junge, Hoersholm (DK);
Jesper Broend, Hoersholm (DK);
Victoria Prebner, Hoersholm (DK)

(73) Assignee: Chr. Hansen A/S, Hoersholm (DK)

( * ) Notice: Subject to any disclaimer, the term of this patent is extended or adjusted under 35 U.S.C. 154(b) by 296 days.

(21) Appl. No.: 18/253,183

(22) PCT Filed: Nov. 16, 2021

(86) PCT No.: PCT/EP2021/081854
§ 371 (c)(1),
(2) Date: May 16, 2023

(87) PCT Pub. No.: WO2022/106418
PCT Pub. Date: May 27, 2022

(65) Prior Publication Data
US 2023/0416673 A1      Dec. 28, 2023

(30) Foreign Application Priority Data
Nov. 17, 2020    (EP) ..................................... 20208167

(51) Int. Cl.
*C12N 1/20*        (2006.01)
*A23C 9/123*       (2006.01)
*C12N 1/205*       (2026.01)
*C12R 1/46*        (2006.01)

(52) U.S. Cl.
CPC ............ *C12N 1/205* (2021.05); *A23C 9/1238* (2013.01); *A23V 2400/123* (2023.08); *A23V 2400/249* (2023.08); *C12R 2001/46* (2021.05)

(58) Field of Classification Search
CPC ... C12N 1/205; A23C 9/1238; C12R 2001/46; A23V 2400/123; A23V 2400/249
USPC ........................................................... 426/43
See application file for complete search history.

(56) References Cited

U.S. PATENT DOCUMENTS

| | | |
|---|---|---|
| 8,865,238 B2 | 10/2014 | Janzen et al. |
| 9,060,524 B2 | 6/2015 | Janzen et al. |
| 9,416,351 B2 | 8/2016 | Janzen et al. |
| 9,562,221 B2 | 2/2017 | Janzen et al. |
| 2012/0164275 A1 | 6/2012 | Janzen et al. |

(Continued)

FOREIGN PATENT DOCUMENTS

| | | |
|---|---|---|
| WO | WO-2011/026863 A1 | 3/2011 |
| WO | WO-2011/092300 A1 | 8/2011 |

(Continued)

OTHER PUBLICATIONS

Xiong, Zhi-Qiang et al.; "Comparison of gal-lac operons in wild-type galactose-positive and -negative *Streptococcus thermophilus* by genomics and transcription analysis"; Journal of Industrial Microbiology & Biotechnology, vol. 46, No. 5; Feb. 4, 2019; pp. 751-758.

*Primary Examiner* — Brent T O'Hern
(74) *Attorney, Agent, or Firm* — Yoshimi D. Barron

(57)          ABSTRACT
The present invention relates to a novel *Streptococcus thermophilus* strain having improved texturizing properties, compositions comprising said strain as well as fermented products manufactured using said strain.

17 Claims, 1 Drawing Sheet
Specification includes a Sequence Listing.

Milk acidifications DSM 17876 and DSM 33677

(56)     References Cited

U.S. PATENT DOCUMENTS

2017/0096635  A1      4/2017   Janzen et al.
2017/0298457  A1*   10/2017   Janzen  ................. A23C 9/1238

FOREIGN PATENT DOCUMENTS

WO          2018/177835  A1    10/2018
WO      WO-2019/122365  A1      6/2019

* cited by examiner

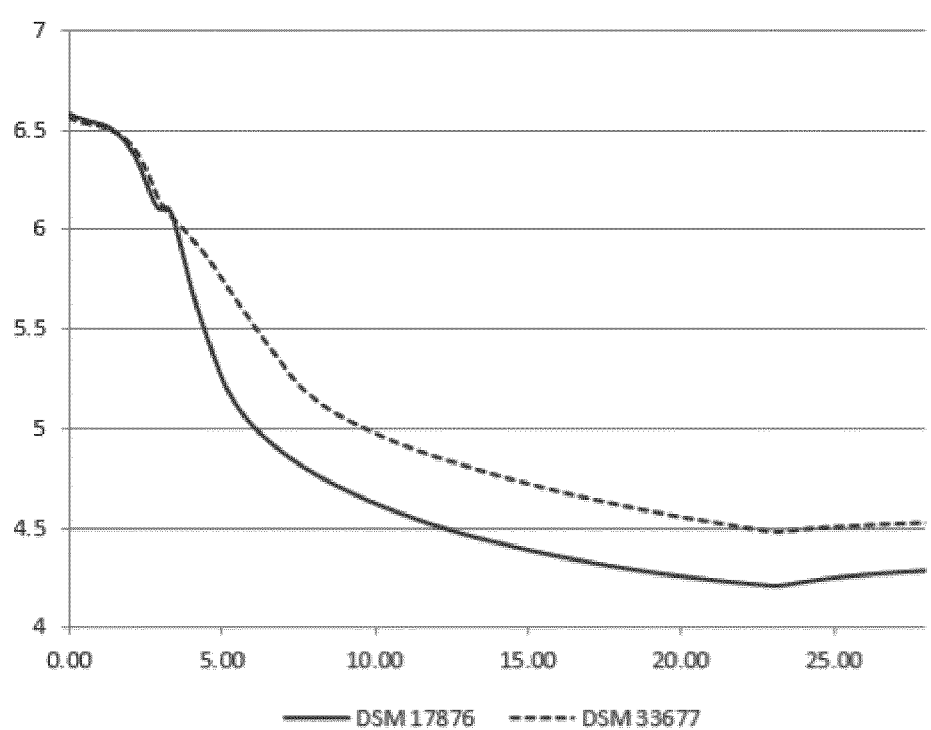

SEQUENCE LISTING

<160> NUMBER OF SEQ ID NOS: 1

<210> SEQ ID NO 1
<211> LENGTH: 1642
<212> TYPE: DNA
<213> ORGANISM: Streptococcus thermophilus

<400> SEQUENCE: 1

```
agaaagtatg atctgcttct acaccaaaaa cttctttaaa cttttctctt aactgtgatg      60
tattcataga atgtatctca cttattcttt ttgtttatac tgaaattgta accactttca     120
catggaaaat caatattttt agatactgtc aataattatg tgtaaacact caagtagagt     180
tgaagaatgt taatcaaata agctttcaag tgtgtcagca cattggccaa accctttatg     240
gatgcgttga ttttgcttga aattataatc ttcaaacagg gtaactaaat aacgttccag     300
agcctcctcg ttaggaaaaa gaaccttctt tttcgtttga cgtttgattt ctttgttaag     360
agactcaatg aggtttgtcg aataaatgct atgccaaatc tggtagggaa actgataaaa     420
agttaaaaga ttatccgtat tctccagact ttccatgact ttcctatact ttggtttcca     480
ttcggcgata aagttctcta aagcttgcac tgccatttct aaattttcag cacgataaat     540
cgttttaaat tgctccagaa taaccgctct atctgctcgt ttcactttac tagctagatt     600
tcgactaata tgaattaagc aacgttgttg tttagctaat gggtaagcct gattgataat     660
ctcttcaagc cccttgaagc catcggtcac tacaagagaa acctgttgga ttccttggtt     720
ttgaagcttg tctaacaggg tggaccaaga agcattgttt tcatttgggg cgatttcata     780
tccaagaaca gccttctgtc cttctggtgt aatgccaagt gcgatatgaa tacattcttt     840
actaacggtt ccacgtctta atggaagata ggttccgtca agaaataaaa cagagtaatt     900
ggcttctaag cttcgctcat gaaaagtagc gacattctcc tgagttgctt ttgagatatt     960
agaaattgtg gcaggactat agtgatgacc atacattcgc tcgatgatat cactaatttc    1020
tcgagtcgtt acaccggttt gatagagttt gataaccatc tcttccaagt ggtcatctcg    1080
acgtccataa gcgggaagca aagctggact aaagttccca ttacgatctc taggaatact    1140
caactgaaca gtcccatatt tggtttcgaa tttccgtgca tagcttccgt tacgactatt    1200
cccagaatta tagcctaatt tatcgtaagg ttcataccct aaaaaggctg ataactctgc    1260
ttgaagcaga tcattcatag ctgtttcaag agaagtacgg aaaaattcat caatatcttg    1320
cttttgggct aggaagttaa gtagttctgt ggtaaactga gtcataggaa taaatctctt    1380
tctagtaatg ttttgcaact ctactataac ggatttattc cttttgtgt ttacacaact    1440 tattttacac tacctatttt attttttttag taaaatatag gtaaaaaata aaagttatgt    1500
tatactgaaa tatgaggagg atactatggc tacattagca gatatcgcaa aattagcagg    1560
tgtatctatt tcaactgttt cacgtgttct taataaagat gaaactcttt ccgtaacaga    1620
ggatactaga catcggatat ta                                            1642
```

LACTIC ACID BACTERIAL STRAIN WITH IMPROVED TEXTURIZING PROPERTIES

CROSS-REFERENCE TO RELATED APPLICATIONS

The present application is the U.S. National Stage of International Application No. PCT/EP2021/081854, filed Nov. 16, 2021, and claims priority to European Patent Application No. 20208167.5, filed Nov. 17, 2020.

TECHNICAL FIELD OF THE INVENTION

The present invention relates to a mutant of *Streptococcus thermophilus*, which was found to have improved texturizing properties while maintaining the growth properties of its parent strain. The present invention, furthermore, relates to compositions, such as a starter culture, comprising the mutant and to fermented products made using this mutant.

BACKGROUND OF THE INVENTION

The food industry uses numerous bacteria, in particular lactic acid bacteria, in order to improve the taste and the texture of foods but also in order to extend the shelf life of these foods. In the case of the dairy industry, lactic acid bacteria are used intensively in order to bring about the acidification of milk (by fermentation) but also in order to texturize the product into which they are incorporated.

Among the lactic acid bacteria used in the food industry, *Streptococcus, Lactococcus, Lactobacillus, Leuconostoc, Pediococcus* and *Bifidobacterium* are predominantly applied. The lactic acid bacteria of the species *Streptococcus thermophilus* (*S. thermophilus*) are used extensively alone or in combination with other bacteria such as *Lactobacillus delbrueckii* subsp *bulgaricus* (*L. bulgaricus*) for the production of food products, in particular fermented products. They are used in particular in the formulation of the ferments used for the production of fermented milks, for example yoghurt. Certain of them play a dominant role in the development of the texture of the fermented product. This characteristic is closely linked to the production of extracellular polymeric that are secreted by the lactic acid bacteria into the surrounding environment.

The current trend in yoghurt is for mild flavor and high texture. Today this is achieved by the use of cultures which produce a mild flavor and the addition of thickeners or protein to give the desired thickness. Yoghurt producers would like to be able to make yoghurt with these properties without the addition of thickening agents. This will help them reduce cost and give a cleaner label. One very attractive way to achieve this would be to have a starter culture which produces a high level of texture.

Many strains of *S. thermophilus* synthesize extracellular polysaccharides (EPS). These molecules may be produced as capsules that are tightly associated with the cell, or they may be liberated into the medium as a loose slime (i.e., "ropy" polysaccharide). Although the presence of exopolysaccharide does not confer any obvious advantage to growth or survival of *S. thermophilus* in milk, in situ production by this species or other dairy lactic acid bacteria typically imparts a desirable "ropy" or viscous texture to fermented milk products. Work has also shown that exopolysaccharide-producing *S. thermophilus* can enhance the functional properties of Mozzarella cheese. For further details see the review article of Broadbent et al. (J. dairy Sci. 86:407-423).

In order to meet the requirements of the industry, it has become necessary to provide novel texturizing strains of lactic acid bacteria, in particular of *S. thermophilus*, for texturizing food products. Especially there is a need for novel texturizing strains of *S. thermophilus* which can be used together with texturizing strains of *Lactobacillus delbrueckii* subsp *bulgaricus*.

SUMMARY OF THE INVENTION

The problem to be solved by the present invention is to provide a novel *S. thermophilus* strain with improved properties in particular in relation to its ability to improve texture of fermented dairy products such as e.g. yogurt and which is useful in present-day highly industrialized dairy production.

In particular, the present invention discloses a novel *S. thermophilus* strain DSM 33677.

Thus, an aspect of the present invention relates to a *Streptococcus thermophilus* strain derived from a galactose-negative mother strain having a Transposase Insertion Element in the Galactose Operon Promotor Region, wherein said *Streptococcus thermophilus* strain becomes galactose-positive by the absence of the Transposase encoding Insertion Element.

In another aspect the present invention relates to a composition comprising the *S. thermophilus* strain DSM 33677.

In a further aspect the present invention relates to a method of producing a fermented product, comprising fermenting a substrate with the *S. thermophilus* strain DSM 33677 or a composition comprising *S. thermophilus* strain DSM 33677.

In yet another aspect the present invention relates to a fermented product obtainable by the method of the present invention.

In another aspect the present invention relates to a fermented product comprising the *S. thermophilus* strain DSM 33677.

Following this, a further aspect relates to the use of the *S. thermophilus* strain DSM 33677 for the manufacture of a fermented product.

BRIEF DESCRIPTION OF THE FIGURES

FIG. 1: Milk acidification graph of strains DSM 17876 and DSM 33677

DETAILED DESCRIPTION OF THE INVENTION

Definitions

Prior to outlining the present invention in more details, a set of terms and conventions is first defined:

The term "milk" is to be understood as the lacteal secretion obtained by milking any mammal, such as cows, sheep, goats, buffaloes or camels. In a preferred embodiment, the milk is cow's milk. The term milk also includes protein/fat solutions made partly or exclusively of plant materials.

The term "milk substrate" may be any raw and/or processed milk material that can be subjected to fermentation according to the method of the invention. Thus, useful milk substrates include, but are not limited to, solutions/suspensions of any milk or milk like products comprising protein, such as whole or low fat milk, skim milk, buttermilk, reconstituted milk powder, condensed milk, dried milk, whey, whey permeate, lactose, mother liquid from crystallization of lactose, whey protein concentrate, or cream.

Obviously, the milk substrate may originate from any mammal, e.g. being substantially pure mammalian milk, or reconstituted milk powder or the milk substrate may originate from a plant material.

Preferably, at least part of the protein in the milk substrate is (i) proteins naturally occurring in mammalian milk, such as casein or whey protein or (ii) proteins naturally occurring in plant milk. However, part of the protein may be proteins which are not naturally occurring in milk.

Prior to fermentation, the milk substrate may be homogenized and pasteurized according to methods known in the art.

"Homogenizing" as used herein means intensive mixing to obtain a soluble suspension or emulsion. If homogenization is performed prior to fermentation, it may be performed so as to break up the milk fat into smaller sizes so that it no longer separates from the milk. This may be accomplished by forcing the milk at high pressure through small orifices.

"Pasteurizing" as used herein means treatment of the milk substrate to reduce or eliminate the presence of live organisms, such as microorganisms. Preferably, pasteurization is attained by maintaining a specified temperature for a specified period of time. The specified temperature is usually attained by heating. The temperature and duration may be selected in order to kill or inactivate certain bacteria, such as harmful bacteria. A rapid cooling step may follow.

Fermentation processes to be used in production of fermented milk products are well known and the person of skill in the art will know how to select suitable process conditions, such as temperature, oxygen, amount and characteristics of microorganism(s) and process time.

Obviously, fermentation conditions are selected so as to support the achievement of the present invention, i.e. to obtain a fermented product such as a dairy or non-dairy product in solid or liquid form (fermented milk product).

In the present context the term "starter culture" is a culture which is a preparation of one or more bacterial strains (such as lactic acid bacteria strains) to assist the beginning of the fermentation process in preparation of fermented products such as various foods, feeds and beverages.

In the present context, a "yoghurt starter culture" is a bacterial culture which comprises at least one *Lactobacillus delbrueckii* subsp *bulgaricus* (*L. bulgaricus*) strain and at least one *Streptococcus thermophilus* (*S. thermophilus*) strain. In accordance herewith, a "yoghurt" refers to a fermented milk product obtainable by inoculating and fermenting a milk substrate with a composition comprising a *L. bulgaricus* strain and a *S. thermophilus* strain.

In the present context, the term "galactose-positive *S. thermophilus* strain" or "gal-positive *S. thermophilus* strain" or "gal+*S. thermophilus* strain" as defined herein means that the pH was reduced by a value of at least 1.0 after 16 hours incubation at 37 degrees C. in M17 with 2% galactose (galactose added as sole carbohydrate), inoculated in an amount of at least $10^4$ cells pr ml of M17.

It has been observed that galactose positive derivatives often exhibited a slower acidification profile and had a higher end pH after more than 20 hours of fermentation (FIG. 1).

Assay I is disclosed in Example 3 and Assay II disclosed in Example 4 discloses selection of galactose-positive *S. thermophilus* based on galactose release.

In the present invention "ability not to excrete galactose" means that the galactose positive strain is not able to excrete any measurable amount of galactose, in particular means that no measurable amount of galactose is detected when tested by assay II.

In the present invention, "ability to excrete galactose but to consume the excreted galactose to completion at most 9 hours" means that the galactose positive strain is able to excrete galactose but to consume the excreted galactose to completion (i.e., to a level below the measurable amount) at most 9 hours after inoculation, in particular means that the galactose positive strain excretes galactose but consumes the excreted galactose to completion (i.e., to a level below the measurable amount) at most 9 hours after inoculation, when tested by assay II.

In an embodiment, the galactose-positive *S. thermophilus* strain as defined herein is characterized by its ability not to excrete galactose, when inoculated at 1% (v/v) into a M17 medium supplemented with 0.5% (wt/wol) of lactose and incubated at 42° C., in particular when tested by assay II.

In an embodiment, the galactose-positive *S. thermophilus* strain as defined herein is characterized by its ability to excrete galactose but to consume the excreted galactose to completion at most 9 hours after being inoculated at 1% (v/v) into a M17 medium supplemented with 0.5% (wt/wol) of lactose and incubated at 42° C., in particular when tested by assay II.

In an particular embodiment, the galactose-positive *S. thermophilus* strain as defined herein is characterized by its ability to excrete galactose but to consume the excreted galactose to completion at most 8 hours after being inoculated at 1% (v/v) into a M17 medium supplemented with 0.5% (wt/wol) of lactose and incubated at 42° C., in particular when tested by assay II.

In the present context, the term "mutant" should be understood as a strain derived, or a strain which can be derived from a strain of the invention (or the mother strain) by means of e.g. genetic engineering, radiation and/or chemical treatment. The mutant can also be a spontaneously occurring mutant. It is preferred that the mutant is a functionally equivalent mutant, e.g. a mutant that has substantially the same, or improved, properties (e.g. regarding viscosity, gel stiffness, mouth coating, flavor, post acidification, acidification speed, and/or phage robustness) as the mother strain. Such a mutant is a part of the present invention. Especially, the term "mutant" refers to a strain obtained by subjecting a strain of the invention to any conventionally used mutagenization treatment including treatment with a chemical mutagen such as ethane methane sulphonate (EMS) or N-methyl-N'-nitro-N-nitroguanidine (NTG), UV light, or to a spontaneously occurring mutant. A mutant may have been subjected to several mutagenization treatments (a single treatment should be understood one mutagenization step followed by a screening/selection step), but it is presently preferred that no more than 20, or no more than 10, or no more than 5, treatments (or screening/ selection steps) are carried out. In a presently preferred mutant less than 1%, less than 0.1, less than 0.01, less than 0.001% or even less than 0.0001% of the nucleotides in the bacterial genome have been replaced with another nucleotide, or deleted, compared to the mother strain.

In the present context, the term "variant" should be understood as a strain which is functionally equivalent to a strain of the invention, e.g. having substantially the same, or improved, properties e.g. regarding viscosity, gel stiffness, mouth coating, flavor, post acidification, acidification speed, and/or phage robustness). Such variants, which may be identified using appropriate screening techniques, are a part of the present invention.

Novel *Streptococcus thermophilus* Strain and Applications Thereof

The inventors have surprisingly identified a *S. thermophilus* strain (i.e. DSM 33677) that fulfils the needs of the industry. The new strain shows improved rheological properties, such a texturization, when applied alone or as part of a mixed culture in a dairy substrate when compared to its mother strain.

*S. thermophilus* strain DSM 33677 have the capacity to be used in e.g. dairy cultures such as yoghurt cultures to obtain improved rheological parameters, such as shear stress (i.e. viscosity) and gel stiffness of the final product. Rheology is closely linked sensory quality of the product and the interplay between rheology and taste in the final product is therefore of outmost importance.

Thus, one aspect of the invention relates to a *Streptococcus thermophilus* strain derived from a galactose-negative mother strain having a Transposase Insertion Element in the Galactose Operon Promotor Region, wherein said *Streptococcus thermophilus* strain becomes galactose-positive by the absence of the Transposase encoding Insertion Element.

In one embodiment the transposase insertion element is located in the galactose operon promotor region sequence corresponding to between nucleotides 133 and 1460 of SEQ ID No: 1.

It may be appreciated that the galactose operon promotor region sequence corresponds to nucleotides 105-133 and 1460-1491 of SEQ ID No: 1. Likewise it may be appreciated that the transposase insertion element sequence corresponds to nucleotides 134-1459 of SEQ ID No: 1 In a further embodiment the mother strain is DSM 17876.

In a further embodiment the invention relates to a *Streptococcus thermophilus* strain DSM 33677 and mutants and variants thereof.

It is contemplated that the mutants and variants show the same or similar shear stress and/or gel firmness characteristics as DSM 33677. In the present context the term "similar shear stress" is to be understood as a range spanning from 10% below the shear stress characteristics of DSM 33677 to 10% above the shear stress characteristics of DSM 33677, the range may also be 9% below/above the shear stress characteristics of DSM 33677, such as 8% below/above of the shear stress characteristics of DSM 33677, e.g. 7% below/above of the shear stress characteristics of DSM 33677, such as 6% below/above of the shear stress characteristics of DSM 33677, e.g. 5% below/above of the shear stress characteristics of DSM 33677, such as 4% below/above of the shear stress characteristics of DSM 33677, e.g. 3% below/above of the shear stress characteristics of DSM 33677, such as 2% below/above of the shear stress characteristics of DSM 33677 or 1% below/above of the shear stress characteristics of DSM 33677.

In the present context the term "similar gel firmness" is to be understood as a range spanning from 10% below the gel firmness characteristics of DSM 33677 to 10% above the gel firmness characteristics of DSM 33677, the range may also be 9% below/above the gel firmness characteristics of DSM 33677, such as 8% below/above of the gel firmness characteristics of DSM 33677, e.g. 7% below/above of the gel firmness characteristics of DSM 33677, such as 6% below/above of the gel firmness characteristics of DSM 33677, e.g. 5% below/above of the gel firmness characteristics of DSM 33677, such as 4% below/above of the gel firmness characteristics of DSM 33677, e.g. 3% below/above of the gel firmness characteristics of DSM 33677, such as 2% below/ above of the gel firmness characteristics of DSM 33677 or 1% below/above of the gel firmness characteristics of DSM 33677.

In the above "characteristics" is to be understood in the context of the definition part where it's stated how to appropriately measure shear stress or gel firmness.

Methods for determining the texture of fermented products such as dairy products include measuring the shear stress (viscosity) or gel stiffness of the fermented product and are readily available and known in the art and exemplified herein.

In a preferred embodiment the *Streptococcus thermophilus* strain DSM 33677 generates a shear stress that is at least 1% improved when compared to its mother strain, such as 2%, e.g. 3%, such as 4%, e.g. 5%, such as 6%, e.g. 7%, such as 8%, e.g. 9%, such as 10% when compared to its mother strain.

In a preferred embodiment the *Streptococcus thermophilus* strain DSM 33677 generates a complex modulus that is at least 1% improved when compared to its mother strain, such as 2%, e.g. 3%, such as 4%, e.g. 5%, such as 6%, e.g. 7%, such as 8%, e.g. 9%, such as 10% when compared to its mother strain.

In a preferred embodiment the *Streptococcus thermophilus* strain DSM 33677 generates a shear stress that is at least 1% improved when compared to its mother strain, such as 2%, e.g. 3%, such as 4%, e.g. 5%, such as 6%, e.g. 7%, such as 8%, e.g. 9%, such as 10% when compared to its mother strain when measured at 300 1/s (Pa) after 16 hours of growth in skimmed milk (0.5% fat) at 43° C. when inoculated in an amount of at least $10^7$ cells per ml of milk.

In a preferred embodiment the *Streptococcus thermophilus* strain DSM 33677 generates a complex modulus that is at least 1% improved when compared to its mother strain, such as 2%, e.g. 3%, such as 4%, e.g. 5%, such as 6%, e.g. 7%, such as 8%, e.g. 9%, such as 10% when compared to its mother strain when measured by oscillation at 1.52 Hz after 16 hours of growth in in skimmed milk (0.5% fat) at 43° C. when inoculated in an amount of at least $10^7$ cells per ml of milk.

By "texture" or "mouthfeel" are meant the product's physical and chemical interaction in the mouth.

In one embodiment of the present invention DSM 33677 is galactose positive.

Besides being galactose-positive *S. thermophilus* strain DSM 33677 has been found to be protease negative (Prt−). Also, it has been found that *S. thermophilus* strain DSM 33677 can be stimulated by the addition of peptides such as but not limited to casein hydrolysates.

Compositions

A further aspect of the present invention relates to a composition comprising or consisting of the *Streptococcus thermophilus* strain DSM 33677.

The composition of the present invention may be provided in several forms. It may be a frozen form, dried form, freeze dried form, or liquid form. Thus, in one embodiment the composition is in frozen, dried, freeze-dried or liquid form.

The composition of the present invention may additionally comprise cryoprotectants, lyoprotectants, antioxidants, nutrients, fillers, flavorants or mixtures thereof. The composition preferably comprises one or more of cryoprotectants, lyoprotectants, antioxidants and/or nutrients, more preferably cryoprotectants, lyoprotectants and/or antioxidants and most preferably cryoprotectants or lyoprotectants, or both. Use of protectants such as cryoprotectants and lyoprotectantare known to a skilled person in the art. Suitable cryoprotectants or lyoprotectants include mono-, di-, tri- and polysaccharides (such as glucose, mannose, xylose, lactose, sucrose, trehalose, raffinose, maltodextrin, starch and gum arabic (acacia) and the like), polyols (such as erythritol, glycerol, inositol, mannitol, sorbitol, threitol, xylitol and the like), amino acids (such as proline, glutamic acid), complex substances (such as skim milk, peptones, gelatin, yeast extract) and inorganic compounds (such as sodium tripolyphosphate). In one embodiment, the composition according to the present invention may comprise one or more cryoprotective agent(s) selected from the group consisting of inosine-5'-monophosphate (IMP), adenosine-5'-monophosphate (AMP), guanosine-5'-monophosphate (GMP), uranosine-5'-monophosphate (UMP), cytidine-5'-monophosphate (CMP), adenine, guanine, uracil, cytosine, adenosine, guanosine, uridine, cytidine, hypoxanthine, xanthine, hypoxanthine, orotidine, thymidine, inosine and a derivative of any such compounds. Suitable antioxidants include ascorbic acid, citric acid and salts thereof, gallates, cysteine, sorbitol, mannitol, maltose.

Suitable nutrients include sugars, amino acids, fatty acids, minerals, trace elements, vitamins (such as vitamin B-family, vitamin C). The composition may optionally comprise further substances including fillers (such as lactose, maltodextrin) and/or flavorants.

In one embodiment of the invention the cryoprotective agent is an agent or mixture of agents, which in addition to its cryoprotectivity has a booster effect.

The expression "booster effect" is used to describe the situation wherein the cryoprotective agent confers an increased metabolic activity (booster effect) on to the thawed or reconstituted culture when it is inoculated into the medium to be fermented or converted. Viability and metabolic activity are not synonymous concepts. Commercial frozen or freeze-dried cultures may retain their viability, although they may have lost a significant portion of their metabolic activity e.g. cultures may lose their acid-producing (acidification) activity when kept stored even for shorter periods of time. Thus viability and booster effect has to be evaluated by different assays. Whereas viability is assessed by viability assays such as the determination of colony forming units, booster effect is assessed by quantifying the relevant metabolic activity of the thawed or reconstituted culture relative to the viability of the culture. The term "metabolic activity" refers to the oxygen removal activity of the cultures, its acid-producing activity, i. e. the production of e.g. lactic acid, acetic acid, formic acid and/or propionic acid, or its metabolite producing activity such as the production of aroma compounds such as acetaldehyde, (a-acetolactate, acetoin, diacetyl and 2,3-butylene glycol (butanediol)).

In one embodiment the composition of the invention contains or comprises from 0.2% to 20% of the cryoprotective agent or mixture of agents measured as % w/w of the material. It is, however, preferable to add the cryoprotective agent or mixture of agents at an amount which is in the range from 0.2% to 15%, from 0.2% to 10%, from 0.5% to 7%, and from 1% to 6% by weight, including within the range from 2% to 5% of the cryoprotective agent or mixture of agents measured as % w/w of the frozen material by weight. In a preferred embodiment the culture comprises approximately 3% of the cryoprotective agent or mixture of agents measured as % w/w of the material by weight. The amount of approximately 3% of the cryoprotective agent corresponds to concentrations in the 100 mM range. It should be recognized that for each aspect of embodiment of the invention the ranges may be increments of the described ranges.

In a further aspect, the composition of the present invention contains or comprises an ammonium salt (e.g. an ammonium salt of organic acid (such as ammonium formate and ammonium citrate) or an ammonium salt of an inorganic acid) as a booster (e.g. growth booster or acidification booster) for bacterial cells, such as cells belonging to the species *S. thermophilus*, e.g. (substantial) urease negative bacterial cells. The term "ammonium salt", "ammonium formate", etc., should be understood as a source of the salt or a combination of the ions. The term "source" of e.g. "ammonium formate" or "ammonium salt" refers to a compound or mix of compounds that when added to a culture of cells, provides ammonium formate or an ammonium salt. In some embodiments, the source of ammonium releases ammonium into a growth medium, while in other embodiments, the ammonium source is metabolized to produce ammonium. In some preferred embodiments, the ammonium source is exogenous. In some particularly preferred embodiments, ammonium is not provided by the dairy substrate. It should of course be understood that ammonia may be added instead of ammonium salt. Thus, the term ammonium salt comprises ammonia (NH3), NH40H, NH4+, and the like.

In one embodiment the composition of the invention may comprise thickener and/or stabilizer, such as pectin (e.g. HM pectin, LM pectin), gelatin, CMC, Soya Bean Fiber/Soya Bean Polymer, starch, modified starch, carrageenan, alginate, and guar gum In one embodiment wherein the microorganism produces a polysaccharide (such as EPS) which causes a high/ropy texture in the acidified milk product the acidified milk product is produced substantially free, or completely free of any addition of thickener and/or stabilizer, such as pectin (e.g. HM pectin, LM pectin), gelatin, CMC, Soya Bean Fiber/Soya Bean Polymer, starch, modified starch, carrageenan, alginate, and guar gum. By substantially free should be understood that the product comprise from 0% to 20% (w/w) (e.g. from 0% to 10%, from 0% to 5% or from 0% to 2% or from 0% to 1%) thickener and/or stabilizer.

The composition may be a mixture or as a kit-of-parts comprising:

i) the *Streptococcus thermophilus* strain DSM 33677, and
ii) a strain belonging to the species *Lactobacillus delbrueckii* subsp *bulgaricus*.

In order to obtain the best combination of acidity, taste, texture of a product such as a dairy product, like yoghurt, a combination of *S. thermophilus* and *Lactobacillus delbrueckii* subsp *bulgaricus* is often applied.

In one embodiment the mixture or kit-of-parts may comprise *S. thermophilus* strain DSM 33677 in combination with *S. thermophilus* strain DSM 22935 and *Lactobacillus delbrueckii* subsp *bulgaricus* strain DSM 22586.

In one embodiment the mixture or kit-of-parts may comprise *S. thermophilus* strain DSM 33677 in combination with *S. thermophilus* strain DSM 24655 and *Lactobacillus delbrueckii* subsp *bulgaricus* strain DSM 33571.

In another embodiment the mixture or kit-of-parts may comprise *S. thermophilus* strain DSM 33677 in combination with *S. thermophilus* strain DSM 24655 and *Lactobacillus delbrueckii* subsp *bulgaricus* strain DSM 24074.

Example 3 shows that a mixed culture comprising *S. thermophilus* and *Lactobacillus delbrueckii* subsp *bulgaricus*.

Probiotic Strains

The term "probiotic bacteria" refers to viable bacteria which are administered in adequate amounts to a consumer for the purpose of achieving a health-promoting effect in the consumer. Probiotic bacteria are capable of surviving the conditions of the gastrointestinal tract after ingestion and colonize the intestine of the consumer.

It will be appreciated that the *Lactobacillus* genus taxonomy was updated in 2020. The new taxonomy is disclosed in Zheng et al. 2020 and will be cohered to herein if nothing else is noticed. For the purpose of the present invention, table 1 presents a list of new and old names of some *Lactobacillus* species relevant to the present invention.

TABLE 1

New and old names of some *Lactobacillus*
species relevant to the present invention

| Old Name | New Name |
|---|---|
| *Lactobacillus reuteri* | *Limosilactobacillus reuteri* |
| *Lactobacillus rhamnosus* | *Lacticaseibacillus rhamnosus* |
| *Lactobacillus salivarius* | *Ligilactobacillus salivarius* |
| *Lactobacillus casei* | *Lacticaseibacillus casei* |
| *Lactobacillus paracasei* subsp. *paracasei* | *Lacticaseibacillus paracasei* subsp. *Paracasei* |
| *Lactobacillus plantarum* subsp. *plantarum* | *Lactiplantibacillus plantarum* subsp. *plantarum* |
| *Lactobacillus fermentum* | *Limosilactobacillus fermentum* |
| *Lactobacillus animalis* | *Ligilactobacillus animalis* |
| *Lactobacillus buchneri* | *Lentilactobacillus buchneri* |
| *Lactobacillus curvatus* | *Latilactobacillus curvatus* |
| *Lactobacillus futsaii* | *Companilactobacillus futsaii* |
| *Lactobacillus sakei* subsp. *sakei* | *Latilactobacillus sakei* subsp. |
| *Lactobacillus pentosus* | *Lactiplantibacillus pentosus* |

In a particular embodiment of the invention the probiotic strain according to the present invention is selected from the group consisting of bacteria of the genus *Lactobacillus*, such as *Lactobacillus acidophilus, Lacticaseibacillus paracasei, Lacticaseibacillus rhamnosus, Lacticaseibacillus casei, Lactobacillus delbrueckii, Lactobacillus lactis, Lactiplantibacillus plantarum, Limosilactobacillus reuteri* and *Lactobacillus johnsonii*, the genus *Bifidobacterium*, such as the *Bifidobacterium longum, Bifidobacterium adolescentis, Bifidobacterium bifidum, Bifidobacterium breve, Bifidobacterium animalis* subsp. *lactis, Bifidobacterium dentium, Bifidobacterium catenulatum, Bifidobacterium angulatum, Bifidobacterium magnum, Bifidobacterium pseudocatenulatum* and *Bifidobacterium infantis*, and the like.

In a particular embodiment of the invention, the probiotic *Lactobacillus* strain is selected from the group consisting of *Lactobacillus acidophilus, Lacticaseibacillus paracasei, Lacticaseibacillus rhamnosus, Lactobacillus casei, Lactobacillus delbrueckii, Lactobacillus lactis, Lactiplantibacillus plantarum, Limosilactobacillus reuteri* and *Lactobacillus johnsonii*.

In a particular embodiment of the invention, the probiotic *Lactobacillus* strain is selected from the group consisting of a *Lacticaseibacillus rhamnosus* strain and a *Lacticaseibacillus paracasei* strain.

In a particular embodiment of the invention, the probiotic strain is *Lacticaseibacillus rhamnosus* strain LGG® deposited as ATCC53103.

In a particular embodiment of the invention, the probiotic strain is *Lacticaseibacillus paracasei* strain CRL 431 deposited as ATCC 55544.

In a particular embodiment of the invention, the probiotic *Bifidobacterium* strain is selected from the group consisting of *Bifidobacterium longum, Bifidobacterium adolescentis, Bifidobacterium 30 bifidum, Bifidobacterium breve, Bifidobacterium animalis* subsp. *lactis, Bifidobacterium dentium, Bifidobacterium catenulatum, Bifidobacterium angulatum, Bifidobacterium magnum, Bifidobacterium pseudocatenulatum* and *Bifidobacterium infantis*.

In a particular embodiment of the invention, the probiotic *Bifidobacterium* probiotic strain is *Bifidobacterium animalis* subsp. *lactis* BB-12 deposited as DSM15954.

The above mixtures or kit-of-parts may be further combined with other lactic acid bacteria such as but not limited to probiotic bacteria. In one embodiment the at least one lactic acid bacteria is selected from the group consisting of *Bifidobacterium* such as *Bifidobacterium animalis* subsp. *Lactis* (e.g. BB-12®), *Lactobacillus acidophilus* (LA-5®), *Lacticaseibacillus 5 rhamnosus* (e.g. LGG®) and combinations thereof. Which *Bifidobacterium, Lactobacillus acidophilus* and/or *Lacticaseibacillus rhamnosus* to apply depending on their application and food to be produced.

In one embodiment the mixture or kit-of-parts may comprise *S. thermophilus* strain DSM 33677 in combination with *S. thermophilus*
strain DSM 22935, *Lactobacillus delbrueckii* subsp *bulgaricus* strain DSM 22586 and at least one lactic acid bacteria selected from the group consisting of *Bifidobacterium, Lactobacillus acidophilus, Lacticaseibacillus rhamnosus* and combinations thereof.

In one embodiment the mixture or kit-of-parts may comprise *S. thermophilus* strain DSM 33677 in combination with *S. thermophilus* strain DSM 24655, *Lactobacillus delbrueckii* subsp *bulgaricus* strain DSM 33571 and at least one lactic acid bacteria selected from the group consisting of *Bifidobacterium, Lactobacillus acidophilus, Lacticaseibacillus rhamnosus* and combinations thereof.

In another embodiment the mixture or kit-of-parts may comprise *S. thermophilus* strain DSM 33677 in combination with *S. thermophilus* strain DSM 24655, *Lactobacillus delbrueckii* subsp *bulgaricus* strain DSM 24074 and at least one lactic acid bacteria selected from the group consisting of *Bifidobacterium, Lactobacillus acidophilus, Lacticaseibacillus rhamnosus* s and combinations thereof.

The above mixtures or kit-of-parts may be further combined with other galactose-positive strains. These strains may for example be DSM32823 and/or DSM32587.

The expression "mixture" means that the *S. thermophilus* strain(s) and the *Lactobacillus delbrueckii* subsp *bulgaricus* strain(s) are physically mixed together. In an embodiment, the *S. thermophilus* strain(s) and the *Lactobacillus delbrueckii* subsp *bulgaricus* strain(s) are in the same box or in the same pouch.

In contrast, the expression "A kit-of-part" comprising *S. thermophilus* strain(s) and the 35 *Lactobacillus delbrueckii* subsp *bulgaricus* strain means that the culture of the *S. thermophilus* strain(s) and the *Lactobacillus delbrueckii* subsp *bulgaricus* strain(s) culture are physically separated but intended to be used together. Thus, the culture of the *S. thermophilus* strain(s) and the *Lactobacillus delbrueckii* subsp *bulgaricus* strain(s) culture are in different boxes or sachets. In an embodiment, the culture of the *S. thermophilus* strain(s) and the *Lactobacillus delbrueckii* subsp *bulgaricus* strain(s) are under the same format, i.e., are in a frozen format, in the form of pellets or frozen pellets, a powder form, such as a dried or freeze-dried powder.

In a particular embodiment of the present invention, the composition comprises from $10^4$ to $10^{12}$ CFU (colony forming units)/g of the *S. thermophilus* strain, such as from $10^5$ to $10^{11}$ CFU/g, such as from $10^6$ to $10^{10}$ CFU/g, or such as from $10^7$ to $10^9$ CFU/g of the *S. thermophilus* strain.

In a particular embodiment the composition further comprises from $10^4$ to $10^{12}$ CFU/g of the *L. bulgaricus* strain, such as from $10^5$ to $10^{11}$ CFU/g, such as from $10^6$ to $10^{10}$ CFU/g, or such as from $10^7$ to $10^9$ CFU/g of the *L. bulgaricus* strain.

*L. bulgaricus, S. thermophilus* and other lactic acid bacteria are commonly used as starter cultures serving a technological purpose in the production of various foods, such as in the dairy industry, such as for fermented milk products. Thus, in another preferred embodiment the composition is suitable as a starter culture.

The composition may be a starter culture such as a yoghurt starter culture.

The composition and/or starter culture may be frozen, spray-dried, freeze-dried, vacuum-dried, air dried, tray dried or in liquid form. Typically, the storage stability of food products can be extended by formulating the product with low water activity. By controlling the water activity (Aw), it is possible to predict and regulate the effect of moisture migration on the product. Therefore, it may be preferred that the water activity (Aw) of the dried compositions herein is in the range from 0.01-0.8, preferably in the range from 0.05-0.4.

A further aspect of the present invention relates to a method of producing a fermented product, comprising fermenting a substrate with the *Streptococcus thermophilus* strain DSM 33677 or a composition according to the present invention.

Depending on the product to be produced the substrate may be a milk substrate. A milk substrate is particularly preferred when fermented milk products such as yoghurt, buttermilk or kefir is the final product.

The milk substrate may be an animal or plant derived product. Thus, in an embodiment the fermented product is a dairy product. The dairy product may be selected from the group consisting of a fermented milk product such as but not limited to yoghurt, buttermilk and kefir or cheese such as but not limited to fresh cheese or pasta filata.

Even though the fermented product and/or the dairy product itself comprise acid and flavor generated during fermentation it may be desired that fermented product and/or the dairy product comprises an ingredient selected from the group consisting of a fruit concentrate, a syrup, a probiotic bacterial culture, a coloring agent, a thickening agent, a flavoring agent, a preserving agent and combinations thereof.

Likewise an enzyme may be added to the substrate e.g. the milk substrate before, during and/or after the fermenting, the enzyme being selected from the group consisting of an enzyme able to crosslink proteins, transglutaminase, an aspartic protease, chymosin, rennet and combinations thereof.

In one embodiment the fermented product may be in the form of a stirred type product, a set type product or a drinkable product.

Clearly another aspect of the present invention relates to a fermented product obtainable by the method of the present invention. An aspect of the present invention is therefore also a fermented product comprising the *Streptococcus thermophilus* strain DSM 33677. The fermented product may be a dairy product.

A last aspect of the present invention relates to the use of the *Streptococcus thermophilus* strain DSM 33677 for the manufacture of a fermented product. Again the fermented product may be a dairy product.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Any listing or discussion of an apparently prior published document in this specification should not necessarily be taken as an acknowledgement that the document is part of the state of the art or is common general knowledge.

Preferences, options and embodiments for a given aspect, feature or parameter of the invention should, unless the context indicates otherwise, be regarded as having been disclosed in combination with any and all preferences, options and embodiments for all other aspects, features and parameters of the invention. This is especially true for the description of the microencapsulated microbial culture and all its features, which may readily be part of the final composition obtained by the method as described herein. Embodiments and features of the present invention are also outlined in the following items and also illustrated by the following non-limiting examples.

Deposits and Expert Solutions

The *Streptococcus thermophilus* strain were deposited at DSMZ (Deutsche Sammlung von Mikroorganismen under Zellkulturen GmbH, Inhoffenstr. 7B, D-38124 Braunschweig, Germany) under the accession number DSM 33677 on 29 Oct. 2020 by Chr. Hansen, Hoersholm, Denmark.

The applicant requests that a sample of the deposited microorganisms stated below may only be made available to an expert, until the date on which the patent is granted.

TABLE 2

Deposits made at a Depositary institution having acquired the status of international depositary authority under the Budapest Treaty on the International Recognition of the Deposit

| Strain | Accession No. | Deposit date |
| --- | --- | --- |
| *Streptococcus thermophilus* | DSM 33677 | 29 Oct. 2020 |

Items

X1. A *Streptococcus thermophilus* strain derived from a galactose-negative mother strain having a Transposase Insertion Element in the Galactose Operon Promotor Region, wherein said *Streptococcus thermophilus* strain becomes galactose-positive by the absence of the Transposase Insertion Element.

X2. The *Streptococcus thermophilus* strain according to item 1, wherein the transposase insertion element is located in the galactose operon promotor region sequence corresponding to between nucleotides 133 and 1460 of SEQ ID No: 1.

X3. The *Streptococcus thermophilus* strain according to item 2, wherein the galactose operon promotor region sequence corresponds to nucleotides 105-133 and 1460-1491 of SEQ ID No: 1.

X4. The *Streptococcus thermophilus* strain according to any of items 1-3, wherein the transposase insertion element sequence corresponds to nucleotides 134-1459 of SEQ ID No: 1

X5. The *Streptococcus thermophilus* strain according to any of items X1-X4, wherein the mother strain is DSM 17876

X6. The *Streptococcus thermophilus* strain according to any of items X1-X5, wherein the *Streptococcus thermophilus* strain is DSM 33677 and mutants and variants thereof.

X7. The *Streptococcus thermophilus* strain DSM 33677 according to any of items X1-X6, wherein the mutants and variants show the same or similar shear stress and/or gel firmness characteristics as DSM 33677.

X8. The *Streptococcus thermophilus* strain DSM 33677 according to to any of items X1-X7, wherein said strain is galactose positive.

Y1. A composition comprising the *Streptococcus thermophilus* strain DSM 33677 according to of any of items X1-X8.

Y2. The composition according to item Y1 comprising, either as a mixture or as a kit-of-parts, i) the *Streptococcus thermophilus* strain DSM 33677 according to any one of items X1-X8; and ii) a strain belonging to the species *Lactobacillus delbrueckii* subsp *bulgaricus*.

Y3. The composition according to any of items Y1-Y2, wherein the composition is a starter culture.

Y4. The composition according to any of items Y1-Y2, wherein the composition and/or starter culture is in frozen, spray-dried, freeze-dried, vacuum-dried, air dried, tray dried or liquid form.

Z1. A method of producing a dairy product, comprising fermenting a substrate with the *Streptococcus thermophilus* strain DSM 33677 according to any one of items X1-X8, or a composition of any of items Y1-Y4.

Z2. The method according to item Z1, wherein the substrate is a milk substrate.

Z3. The method according to any one of items Z1-Z2, wherein the milk substrate is an animal or plant derived product.

Z4. The method according to any one of items Z1-Z3, wherein the fermented product is a dairy product.

Z5. The method according to item Z4, wherein the dairy product is selected from the group consisting of a fermented milk product (e.g. yoghurt, buttermilk or kefir) or a cheese (e.g. fresh cheese or pasta filata).

Z6. The method according to any one of items Z1-Z5, wherein the fermented product further comprises an ingredient selected from the group consisting of a fruit concentrate, a syrup, a probiotic bacterial strain or culture, a colouring agent, a thickening agent, a flavouring agent, a preserving agent and mixtures thereof.

Z7. The method according to any one of items Z1-Z5, wherein an enzyme is added to the substrate before, during and/or after the fermenting, the enzyme being selected from the group consisting of an enzyme able to crosslink proteins, transglutaminase, an aspartic protease, chymosin, rennet and combinations thereof.

Z8. The method according to any one of items Z1-Z7, wherein the fermented product is in the form of a stirred type product, a set type product, or a drinkable product.

Q1. A fermented product obtainable by the method according to any one of items Z1-Z8.

Q2. The fermented product according to item Q1, wherein the fermented product is a dairy product.

P1. A fermented product comprising the *Streptococcus thermophilus* strain DSM 33677 according to of any of items X1-X8.

P2. The fermented product according to item P1, wherein the fermented product is a dairy product.

W1. Use of the *Streptococcus thermophilus* strain DSM 33677 according to of any one of items X1-X8 for the manufacture of a fermented product.

W1. The use according to claim W1, wherein the fermented product is a dairy product.

---

Sequence listing

```
SEQ ID NO 1: DNA sequence from DSM 17876 covering galK start, gal operon
promoter with insertion sequence and start of galR
AGAAAGTATGATCTGCTTCTACACCAAAAACTTCTTTAAACTTTTCTCTTAACTGTGATGTATTCATAGAA
TGTATCTCACTTATTCTTTTTGTTTATACTGAAATTGTAACCACTTTCACATGGAAAATCAATATTTTTAGA
TACTGTCAATAATTATGTGTAAACACTCAAGTAGAGTTGAAGAATGTTAATCAAATAAGCTTTCAAGTGT
GTCAGCACATTGGCCAAACCCTTTATGGATGCGTTGATTTTGCTTGAAATTATAATCTTCAAACAGGGTA
ACTAAATAACGTTCCAGAGCCTCCTCGTTAGGAAAAAGAACCTTCTTTTTCGTTTGACGTTTGATTTCTTT
GTTAAGAGACTCAATGAGGTTTGTCGAATAAATGCTATGCCAAATCTGGTAGGGAAACTGATAAAAAGT
TAAAAGATTATCCGTATTCTCCAGACTTTCCATGACTTTCCTATACTTTGGTTTCCATTCGGCGATAAAGT
TCTCTAAAGCTTGCACTGCCATTTCTAAATTTTCAGCACGATAAATCGTTTTAAATTGCTCCAGAATAACC
GCTCTATCTGCTCGTTTCACTTTACTAGCTAGATTTCGACTAATATGAATTAAGCAACGTTGTTGTTTAGC
TAATGGGTAAGCCTGATTGATAATCTCTTCAAGCCCCTTGAAGCCATCGGTCACTACAAGAGAAACCTGT
TGGATTCCTTGGTTTTGAAGCTTGTCTAACAGGGTGGACCAAGAAGCATTGTTTTCATTTGGGGCGATTT
CATATCCAAGAACAGCCTTCTGTCCTTCTGGTGTAATGCCAAGTGCGATATGAATACATTCTTTACTAAC
GGTTCCACGTCTTAATGGAAGATAGGTTCCGTCAAGAAATAAAACAGAGTAATTGGCTTCTAAGCTTCG
CTCATGAAAAGTAGCGACATTCTCCTGAGTTGCTTTTGAGATATTAGAAATTGTGGCAGGACTATAGTGA
TGACCATACATTCGCTCGATGATATCACTAATTTCTCGAGTCGTTACACCGGTTTGATAGAGTTTGATAA
CCATCTCTTCCAAGTGGTCATCTCGACGTCCATAAGCGGGAAGCAAAGCTGGACTAAAGTTCCCATTAC
GATCTCTAGGAATACTCAACTGAACAGTCCCATATTTGGTTTCGAATTTCCGTGCATAGCTTCCGTTACG
```

-continued

Sequence listing

```
ACTATTCCCAGAATTATAGCCTAATTTATCGTAAGGTTCATACCCTAAAAAGGCTGATAACTCTGCTTGA
AGCAGATCATTCATAGCTGTTTCAAGAGAAGTACGGAAAAATTCATCAATATCTTGCTTTTGGGCTAGGA
AGTTAAGTAGTTCTGTGGTAAACTGAGTCATAGGAATAAATCTCTTTCTAGTAATGTTTTGCAACTCTACT
ATAACGGATTTATTCCTTTTTGTGTTTACACAACTTATTTTACACTACCTATTTTATTTTTTTAGTAAAATAT
AGGTAAAAAATAAAAGTTATGTTATACTGAAATATGAGGAGGATACTATGGCTACATTAGCAGATATCGC
AAAATTAGCAGGTGTATCTATTTCAACTGTTTCACGTGTTCTTAATAAAGATGAAACTCTTTCCGTAACAG
AGGATACTAGACATCGGATATTA

Start nucleotide galK gene (minus strand): 67
Transposase encoding Insertion sequence includes nucleotides: 134-1459
Start nucleotide galR gene (plus strand): 1526
Promoter region on both sides of insertion element (IS element sits in
the middle):
Part 1: 105-133
Part 2: 1460-1491
```

EXAMPLES

Example 1: Selection of a Galactose Positive Mutants of *Streptococcus thermophilus* Strain DSM 17876

Isolation of Galactose Fermenting Strain

Mutants were isolated as galactose fermenting mutant of *S. thermophilus* strain DSM 17876. The DSM 17876 cells were neither mutagenized with any mutagenic compound nor by UV light prior to the mutant isolation step. The isolated strains resemble therefore spontaneous galactose-positive mutants of DSM 17876.

Prior to the mutant isolation DSM 17876 was streaked on M17 agar plates with 2% galactose (M17-gal plates). DSM 17876 did not grow on galactose as sole carbohydrate source.

Typically galactose fermenting mutants are isolated by plating a culture of *S. thermophilus* strain on M17-2% gal plates and then pick the colonies that will appear after two days of growth at 37° C. This method was not working for the isolation of galactose fermenting mutants of DSM 17876. Even inoculation in liquid M17+ 2% galactose did not result in any significant growth.

*S. thermophilus* DSM 17876 will grow on M17+lactose. In order to generate a high number of growing cells the strain was inoculated in M17 with 0.2% lac+2% gal. The lactose enabled a high number of cells to grow. When lactose is consumed only those cells that naturally are galactose positive in the pool of cells can continue to grow. After 24 hours, a more dense culture was obtained. From this culture 100 μl was inoculated into fresh M17 medium with 2% galactose. From this culture a dilution of the culture was plated on M17-gal plates and after 24 hours, a number of colonies were picked and re-streaked 3 time on M17-gal plates to purify the strains. Finally one clone was selected and tested further. The DNA was isolated and genome sequenced. The new strain was deposited as DSM 33677. Compared to DSM 17876, DSM 33677 acidified B-milk (skim milk powder at a level of dry matter of 9.5% (w/v) reconstituted in distilled water and pasteurized at 99° C. for 30 min, followed by cooling to 30° C.) (FIG. 1).

Genome sequencing DSM 17876 and DSM33677 showed why it was more difficult to select a galactose fermenting mutant of DSM 17876. DSM 17876 is galactose-positive because the promoter upstream of the galactose operon contains an transposase insertion element in the promoter region that disables transcription. In DSM 33677 this insertion element has jumped out and left a promoter open for transcription. This result in transcription of the gal operon and the strain becomes galactose-positive.

Example 2: Production of Plain Stirred Yogurt with a Blend Comprising DSM 33677

Materials and Methods

Milk base: 4.0% protein, 1.5% fat. Fresh milk with Arla Medium Heat Skimmed milk powder (SMP)

Cultures:

Culture 2 (*L bulgaricus* strain DSM 33571 and *S. thermophilus* strains DSM 33677 and DSM 24655), and F-DVS YoFlex® Premium 1.0, a proprietary prior art culture comprising one *L. bulgaricus* strain in combination with 2 different *S. thermophilus* strains.

| | |
|---|---|
| Fermentation scale | 3 L |
| Mixing of powder and re-hydration of milk base | Disperse powder in cold milk (<10° C.), heat to 58° C. (±2° C.) and re-hydrate for 1 hour at 58° C. (±2° C.) with stirring |
| Homogenization | 200/50 bar at 65° C. |
| Pasteurization | 95° C. for 5 min |
| Culture inoculation | 500 U/2500 L (min. 1E10 cfu/g), inoculation at 43° C. |
| Fermentation temperature | 43° C. |
| Cut pH | pH 4.55 |
| Post treatment | Apply 2 bar before plate heat exchanger with outlet temperature set to 20° C. (±2° C.) |

Results

Complex Modulus G*—Correlating to Gel Firmness

Complex Modulus G* is evaluated by oscillation measurement using ASC rheometer model DSR502 from Anton Paar. The method is based on an oscillation step, where the sample is oscillated between two surfaces, with the upper geometry (bob) moving and the lower cup remaining stationary. The oscillation is performed from 0.5-8 Hz at constant strain. For these evaluations the results are extracted from measurements at 1.52 Hz. Samples are placed at 13° C. for 1 hour prior to measuring. Each sample is gently stirred with a spoon 5 times from bottom to top to assure a homogenous sample. The rheology cups are filled until the line and placed in the sample magazine. Samples are measured in duplicates using two separate yogurt cups. Measurements are conducted at day +7 and temperature of measurement is set to 13° C. Samples are stored at 5° C.

until the day of measurement. As there are three productions included for these results there is in total 6 data points.

TABLE 3

Gel firmness results measured by Complex Modulus G* by Oscillation at 1.52 Hz. The results are shown as average results, including the standard deviation from 3 replicate trials in ATC where samples were measured in duplicates. Measurements were conducted at day +7 adjusting the temperature to 13° C.

| Culture | Average results Complex Modulus G* (Pa) | STDev |
|---|---|---|
| F-DVS YoFlex ® Premium 1.0 | 143.5 | 7.1 |
| Culture 2 | 154.8 | 7.0 |

Shear Stress—Correlating to Mouth Thickness

Shear stress is measured by using ASC rheometer model DSR502 from Anton Paar. The method is using a rotational step which is based on a rotational deformation on the sample, from 10-3 s-1 to 300 s-1, and then back to 10-3 s-1. The corresponding shear stress is measured. For these results, four shear rates (0.3; 30; 135; 300 s-1) are extracted from the flow curve (see Table 4). Samples are placed at 13° C. for 1 hour prior to measuring. Each sample is gently stirred with a spoon 5 times from bottom to top to assure a homogenous sample. The rheology cups are filled until the line and placed in the sample magazine. Samples are measured in duplicates using two separate yogurt cups. Measurements are conducted at day +7 and temperature of measurement is set to 13° C. Samples are stored at 5° C. until the day of measurement. As there are three productions included for these results there is in total 6 data points.

TABLE 4

Shear stress results measured by Anton Paar rheometer. The results are shown as average results, including the standard deviation from 3 replicate trials in ATC where samples were measured in duplicates. Measurements were conducted at day +7 adjusting the temperature to 13° C.

| Culture | 0.3 s-1 | 30 s-1 | 135 s-1 | 300 s-1 |
|---|---|---|---|---|
| | | AVERAGE | | |
| F-DVS YoFlex ® Premium 1.0 | 4.8 | 25.7 | 47.9 | 54.2 |
| Culture 2 | 5.3 | 38.4 | 64.1 | 67.6 |
| | | STDev | | |
| F-DVS YoFlex ® Premium 1.0 | 0.2 | 1.3 | 0.8 | 0.7 |
| Culture 2 | 0.2 | 2.8 | 4.6 | 5.0 |

Example 3: Selection of Galactose-Positive *S. thermophilus* Based on pH (Assay I)

Assay I is as follows:

*S. thermophilus* strains characterized as galactose-positive (i.e., described as able to grow on a medium comprising galactose as the only source of carbohydrates) were grown overnight at 37° C. in M17 supplemented with sucrose 30 g/L;

the culture was washed (v/v) in tryptone-salt solution (tryptone 1 g/L, NaCl 8.5 g/L) as follows: the culture was centrifuged at 4000 rpm for 5 minutes; the pellet was resuspended in 10 ml of tryptone-salt solution the washed culture was inoculated at 1% (v/v) into 150 ml of M17 oxoid supplemented with galactose 30 g/L;

the inoculated medium was incubated at 43° C. for 24 hours, and its pH monitored using a CINAC system (Alliance Instruments, France; pH electrode Mettler 405 DPAS SC, Toledo, Spain);

the pH was measured and recorded every 5 minutes. Using the CINAC v2.07 software, the following parameters were specifically calculated: the time to reach a pH of 5.2 and the slope between pH 6.4 and pH 5.6 (pH/minute) [Slope pH6.4-5.6].

It is expected that it is not sufficient that the tested strain be able to grow on a galactose medium. In addition, this strain must be able to reach the pH of 5.2 in a minimal time, i.e., to optimally consume the galactose of the medium in a manufacturing time which is industrially acceptable. Thus, by assay I, a galactose-positive *S. thermophilus* strain was considered to be suitable for the invention when:

reaching a pH of 5.2 in less than 5 hours, when tested by assay I (i.e., decreasing the pH of the inoculated medium to 5.2 in less than 5 hours when tested by assay I); and optionally with an average speed of acidification of at least 0.01 pH/min between pH 6.4 and 5.6, when tested by assay I.

Example 4: Selection of Galactose-Positive *S. thermophilus* Based on Galactose Release (Assay II)

Assay II is as follows:

*S. thermophilus* strains characterized as galactose-positive are grown 12 hours at 42° C. in M17 supplemented with 0.5% (wt/vol) of lactose [1% (v/v) inoculation]; this step is repeated a second time in the same conditions;

the culture is inoculated at 1% (v/v) into a M17 medium supplemented with 0.5% (wt/vol) of lactose, and the inoculated medium is incubated at 42° C. up to 10 hours;

during fermentation, samples are withdrawn every 30 minutes to determine the galactose concentration; samples are centrifuged at 14000×g for 5 minutes, filtered sterilized through Phenex nylon 0.45 pm-pore size×15 mm diameter filters (Phenomenex®) and stored at −20° C. until further analysis; 10 m I of each sample are injected on an Agilent® 1 100 HPLC. The elution is done through isocratic mode with pure H2O at 0.6 ml/min. Sugars are separated in 40 minutes onto a Pb2+ ion exchange column (SP0810 Shodex™ 300 mm×8 mm×7 pm). The concentration of galactose (if any) is determined (g/L). Concentration of galactose below 0.05 g/L is considered not measurable.

In addition to or alternatively to the time to reach a pH of 5.2, among galactose positive strains, it is expected that the strains either not able to excrete galactose by assay II or able to excrete galactose into the medium but able to consume it to completion by assay II would offer an interesting behavior in terms of galactose catabolism into a dairy substrate. Thus, by assay II, a galactose-positive *S. thermophilus* strain is considered to be suitable for the invention when:

no measurable amount of galactose is detected, when tested by assay II; or the strain excretes galactose but consumes the excreted galactose to completion (i.e., to a level below the measurable amount) at most 9 hours after inoculation, when tested by assay II.

The invention claimed is:

1. An isolated mutant *Streptococcus thermophilus* strain derived from a galactose-negative mother strain having a transposase insertion element in its galactose operon promotor region, wherein said mutant *Streptococcus thermophilus* strain lacks a transposase insertion element in its galactose operon promotor region and is galactose-positive, wherein the galactose-negative mother strain is the *Streptococcus thermophilus* strain deposited at Deutsche Sammlung von Mikroorganismen und Zellkulturen GmbH (Braunschweig, Germany) (DSMZ) under accession number DSM 17876.

2. The mutant *Streptococcus thermophilus* strain according to claim 1, wherein the transposase insertion element of the mother strain is located in the galactose operon promotor region at a site corresponding to between nucleotides 133 and 1460 of the nucleotide sequence of SEQ ID NO: 1.

3. The mutant *Streptococcus thermophilus* strain according to claim 2, wherein the galactose operon promotor region comprises a nucleotide sequence comprising nucleotides 105-133 and 1460-1491 of the nucleotide sequence of SEQ ID NO: 1.

4. The mutant *Streptococcus thermophilus* strain according to claim 1, wherein the transposase insertion element of the mother strain comprises a nucleotide sequence comprising nucleotides 134-1459 of the nucleotide sequence of SEQ ID NO: 1.

5. The mutant *Streptococcus thermophilus* strain according to claim 1, wherein the mutant *Streptococcus thermophilus* strain is selected from an *Streptococcus thermophilus* strain deposited at DSMZ under accession number DSM 33677 and mutants and variants thereof.

6. A composition comprising the mutant *Streptococcus thermophilus* strain according to claim 1 and a cryoprotectant.

7. The composition according to claim 6, further comprising a strain of species *Lactobacillus delbrueckii* subsp *bulgaricus*.

8. A method of producing a dairy product, comprising fermenting a substrate with the mutant *Streptococcus thermophilus* strain according to claim 1.

9. A fermented product obtained by the method according to claim 8.

10. The fermented product according to claim 9, wherein the fermented product is a dairy product.

11. A fermented product comprising the mutant *Streptococcus thermophilus* strain according to claim 1.

12. The mutant *Streptococcus thermophilus* strain according to claim 1, wherein the mutant strain is *Streptococcus thermophilus* strain DSM 33677.

13. The composition according to claim 6, wherein the mutant *Streptococcus thermophilus* strain is *Streptococcus thermophilus* strain DSM 33677.

14. The method according to claim 8, wherein the mutant *Streptococcus thermophilus* strain is *Streptococcus thermophilus* strain DSM 33677.

15. The fermented product according to claim 11, wherein the mutant *Streptococcus thermophilus* strain is *Streptococcus thermophilus* strain DSM 33677.

16. A product comprising as a kit-of-parts:
(i) the mutant *Streptococcus thermophilus* strain according to claim 1; and
(ii) a strain of species *Lactobacillus delbrueckii* subsp *bulgaricus*.

17. The product according to claim 16, wherein the mutant *Streptococcus thermophilus* strain is *Streptococcus thermophilus* strain DSM 33677.

* * * * *